United States Patent [19]

Feist

[11] 4,208,914
[45] Jun. 24, 1980

[54] METHOD FOR DETERMINING THE INTERACTION BETWEEN A CHEMICAL SOLUTION AND AN OBJECT IMMERSED IN THE SOLUTION

[75] Inventor: Wolf-Dieter Feist, Karlsfeld, Fed. Rep. of Germany

[73] Assignee: Motoren-und Turbinen-Union München GmbH, Fed. Rep. of Germany

[21] Appl. No.: 922,655

[22] Filed: Jul. 7, 1978

[30] Foreign Application Priority Data

Jul. 7, 1977 [DE] Fed. Rep. of Germany ....... 2730622

[51] Int. Cl.$^2$ ............................................. G01N 29/00
[52] U.S. Cl. ................................................... 73/590
[58] Field of Search ............... 73/590, 587; 134/57 R, 134/113; 23/230 C; 422/53

[56] References Cited

U.S. PATENT DOCUMENTS

| | | | |
|---|---|---|---|
| 2,614,645 | 10/1952 | Wilhelm | 73/590 |
| 3,654,072 | 4/1972 | Massa | 73/590 |
| 3,946,600 | 3/1976 | Rettig et al. | 73/590 |

*Primary Examiner*—Anthony V. Ciarlante
*Attorney, Agent, or Firm*—Craig & Antonelli

[57] ABSTRACT

A process for determining the interactions between a solution and a body immersed in the solution, comprising the steps of measuring the sound emission from the body, such as sound waves in the ultrasonic range, while the solution and body are interacting and using this measurement to determine the interaction. The process can be used, inter alia, during the chemical removal of material from a body by a solution, such as chemical etching, to determine the degree of exhaustion of the solution. Moreover, the sound emission can be used in the control of further interaction between the solution and body.

10 Claims, 1 Drawing Figure

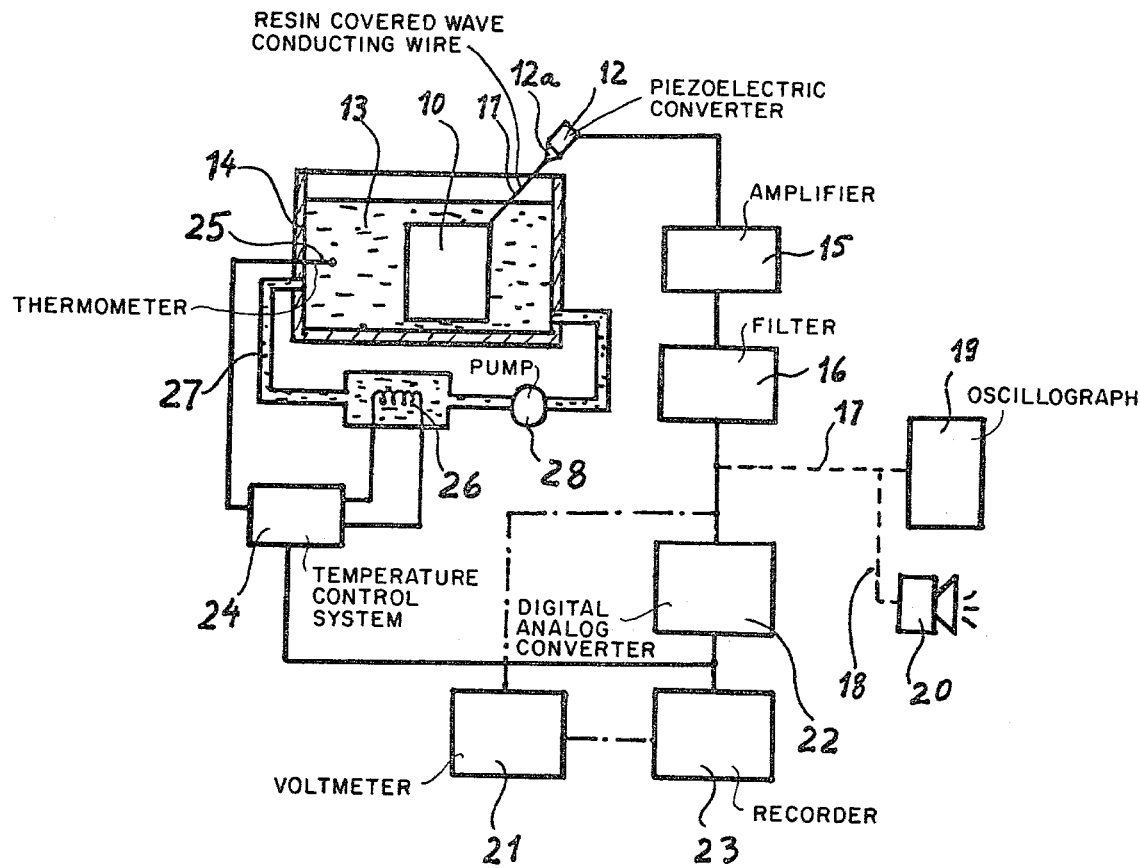

METHOD FOR DETERMINING THE INTERACTION BETWEEN A CHEMICAL SOLUTION AND AN OBJECT IMMERSED IN THE SOLUTION

The present invention relates to a method of determining the interactions between a chemical solution and an object immersed in the solution. In particular, the invention involves a method of determining these interactions through the use of the sound emission from the object during the interaction.

The degree of exhaustion of process solutions such as they are used for the most diverse surface treatments of materials, particularly of metals, has in many cases been determined from rather subjective aspects (experience of supervisor). This is attended by the risk of the solutions no longer being fully effective, i.e. of not or not entirely doing the job, or of the solutions being replaced prematurely, involving unnecessary costs of chemicals and decontamination plus unnecessary environmental burden.

In electrolytic processes the electric current can be used as a regulating variable for the process. In the chemical removal of material this possibility has so far been prevented for the reason that this process takes place in the absence of electric current.

In the chemical removal of material the final size has so far been achieved by measuring after about 80% of the process time, the material removal on one or more inspection parts, from which the time still required is then computed by extrapolation. This method is wasteful and difficult to automate.

It is common knowledge that in various processes or reactions in and on materials, body sound waves are emitted which run in the ultrasonic range and can be picked up by means of probes. This phenomenon is generally termed sound emission. The measurements are taken in the 50 KHz to 2 MHz frequency range. The signals are amplified and processed from various aspects. In the corrosion of metals, e.g., measurable sound is known to be emitted. This is seen as being connected with the development of hydrogen.

In accordance with the present invention this phenomenon is used in the determination of the interaction taking place between a chemical solution and an object immersed in said solution. On material, particularly metals, treated in process solutions this involves various processes or reactions which produce sound emission and which in intensity or in their occurrence per se vary with the condition of the solution. Conceivable sources of emission would thus be: development of hydrogen, dissolution of individual elements and thus shift of internal microstresses, microcracking, intergranular attack, stress corrosion, diffusion of elements, and certainly a few more. For example, in a process of chemical removal where a work piece or a material sample is brought from oversize to finishing size, the ultrasonic waves emitted as a result of the removal process are determined to serve as a measure of the amount of material removed for indication when the final or finishing dimension is reached or for using the sound waves as a regulating variable, if necessary, to control the removal process.

If it is the intention to determine the degree of exhaustion of a process solution, the sound waves emitted in the reaction between the solution and the object immersed in the solution serve as a measure of the degree of exhaustion or of the remaining reactivity.

In a particular aspect of this invention the degree of exhaustion is determined by withdrawing a sample from the process solution to be tested and bringing it to the normal process temperature. An inspection material, which normally would be the material for which the effectiveness of the solution is to be determined, is suspended into the solution sample as a test piece of standardized size. Welded to said material sample is a wire of the same material, which wire acts as a wave conductor to carry the body sound waves to the probe outside the solution. The signals received then give, after suitable processing, a direct measure of the effectiveness by comparison with values determined in preceding tests. Conceivably the effectiveness can be determined during the process also in the main solution proper and intervention can be made in the process under way, i.e. the process can be controlled, by way of the process temperature and/or by variations in the concentration of the solution.

The method of the present invention is suitable for use in the electrolytical and cleaning areas. It can find use also in wide areas of the manufacturing industry wherever use is made of process solutions.

In the chemical removal of material a wire of identical material is attached to one or more work pieces or material samples, which wire acts as a wave conductor to establish communication with the probe outside the solution. The wave conductor may be up to several meters in length. As the work piece is being treated, it emits sound impulses, the number and/or intensity of which serves as a measure of the amount of material removed.

More particularly this measurable variable can be used to control the process via, e.g., the temperature or concentration of the solution, for optimum removal conditions. Also, when defects arise, such as cracking and/or the formation of pores, these will intensify and/or vary (e.g., other frequencies) the emissions and can so be identified directly during the process.

The present invention provides a method for use in the chemical removal of material for continuously determining the amount of material removed during the process by means of a measurable variable and for directly intervening, if necessary, in the process by changing parameters.

In order that the invention may be more readily understood examples will be described with reference to the accompanying drawing.

A body 10 of metal or any metal alloy such as iron, aluminium, cobalt basis alloys etc to be subjected to an interaction between a solution and the surface of the body is covered with resine on the surface parts where no interaction with the solution is desired.

A wave conducting wire 11 of the same material as the body is welded on the body 10 and covered with resine if also immersed in the solution. On the other end of the wire is welded a conical piece 12a of the same material which is mounted on a known piezoelectric converter 12.

The body 10 is then immersed in the solution 13 contained in the container 14 and a chemical process as for instance oxidation, hydrogenation, dissolution of selected elements, will start.

It has been found that these interactions or processes, where energy is released, produce supersonic signals in the body 10. These signals are conducted through the wire 11 to the piezoelectric converter where the sound signals are converted into electric impulses. The electric signals are then amplified and filtered with an amplifier 15 and a frequency filter 16 respectively of the types known in the art.

These signals—which are proportional to the solution concentration, or to the bath temperature or are dependent to the degree of the reaction process, of the etching process etc—are now prepared to be processed in one or more of various possible aspects.

Through the dotted lines 17 and 18 the signal comming from the filter 16 is supplied to an oscillograph 19 for projecting the signals on a screen or to a loud speaker 20 respectively, where the electrical signals are converted in acoustic signals.

Other ways of detecting the sound emission from the body 10 are using a voltmeter 21 or an digital analog converter 22 of known types and recording their outputs on a x versus time recorder 23.

The output signal of the digital converter 22 can be used also to command a control for supplying fresh solution when necessary, to control the bath temperature etc. In the drawing is shown a temperature control system 24 of known type being associated to a thermometer 25. In response to the process evolution and consequently to the output signals of the digital converter 22 the control 24 will set a heater 26 in operation in order to heat the solution flowing through the container 14 and a pipe 27 provided with a pump 28 till the temperature of the bath has raised to the desired value.

By way of example the control of a scaling process of a TiA16V4 housing of a turbojet engine is described.

The housing is first cleaned mechanically using a fat-dissolving cleanser, such as $CaCO_3$ dissolved in pure Methanol. The cleanser is washed up and the clean housing 10 with the welded conducting wire 11 (1 m long, 1 mm diameter) is introduced in the container 12. The housing having a dimension of $50 \times 25 \times 1$ $mm^3$.

The scaling process of TiA16V4 is performed in two steps. In a first step the oxide to be removed is processed and then etched in a second step.

For the first step is used a bath 13 containing 700 g/l caustic soda and 3 g/l dichromate at 130°–140° C. This solution reacts with the oxide on the surface of the body 10 emitting sound waves which are converted to electrical signals by means of a conventional resonance converter 12 with about 200 KHz resonance frequency and a sensibility of about 70 dB related to 1 v/$\mu$ bar at 200 KHz. The output signal is amplified about 85 dB and filtered in a range of 100–300 KHz.

The signals are detected in one of the ways described above and controlled. When the intensity of the signals decrease under a predetermined value the reaction has come to the end and the body is removed from the first bath.

For the second step is used an etching bath containing 400 g/l $HNO_3$, 40 g/l HF and damping product at room-temperature. The same sound detecting system of the first step is used. If the signal-intensity decreases a certain value it might be necessary to renew the bath.

In an another example an heat resisting body of Ni-basis-alloy is deformed by etching and the etching process is controlled by sound-emission detection.

The body, for example a thrust reverser of a turbojet engine, is ungreased as in the previous example and covered with varnish on the surface parts which are not to be etched. The free surface parts are firstly activated with nitric acid. The body 10 is then immersed in a bath 13 containing hydrochloric acid, nitric acid, iron-3-chloride and charcoal.

The reactivity of the activating process and the etching process are respectively controlled by means of the emitted sound waves as indicated above.

With the control according to the invention the body must not be removed several times from the etching bath for measurements and reactivated every time before immersing the body again in the etching solution.

What is claimed is:

1. Method for determining the amount of material removed from an object comprising said material, in chemically removing at least a portion of said material from said object in reducing said object from oversize to a finishing size, wherein said object is immersed in a solution which chemically removes said material from said object, comprising the steps of:

(a) acoustically sensing the sound waves in the ultrasonic wave range of 50 KHz to 2 MHz emitted from the object immersed in said solution while said material is being chemically removed from said object, by means of probes, said waves being acoustically sensed by attaching a wire made of said material to said object and also attaching said wire to a probe, whereby said wire acts as a wave conductor from said object to said probe;

(b) amplifying the sensed sound waves; and (c) interpreting the amplified sound waves to determine the amount of material removed from said object.

2. Method of claim 1, wherein the amplified sound waves are interpreted to indicate when the finishing dimension is reached.

3. Method of claim 1, wherein the material is a metal or metal alloy.

4. Method of claim 1, wherein the amplified sound waves are interpreted to indicate when defects arise in said object while said material is being removed from said object.

5. Method of claim 1, characterized in that the sound emission is used in the control of the material removal process.

6. Method for determining the degree of exhaustion of a chemical solution, wherein said chemical solution has an object immersed therein, said object being a standard-sized sample, and wherein said chemical solution reacts with the material of which said object is comprised, comprising the steps of:

(a) acoustically sensing the sound waves in the ultrasonic wave range of 50 KHz to 2 MHz emitted from the object while the object is immersed in said chemical solution and during the reacting of the chemical solution with the object, by means of probes, said sound waves being acoustically sensed by attaching a wire made of said material to said object and also attaching said wire to a probe, whereby said wire acts as a wave conductor from said object to said probe;

(b) amplifying the sensed sound waves; and (c) interpreting the amplified sound waves to determine the degree of exhaustion of the chemical solution.

7. Method of claim 6, wherein said object is comprised of a metallic material.

8. Method of claim 6, wherein said object is comprised of a material to be reacted with said solution, whereby the effectiveness of said chemical solution for reacting with said material can be determined.

9. Method of claim 1 or 6, wherein the probe is positioned outside of the solution.

10. Method of claim 6, characterized in that said chemical solution is a sample withdrawn from a main solution, whereby the degree of exhaustion of the main solution can be determined by measuring the degree of exhaustion of a sample thereof.

* * * * *